(12) United States Patent
Danicher et al.

(10) Patent No.: US 9,458,212 B2
(45) Date of Patent: Oct. 4, 2016

(54) NANOPARTICLES CONTAINING A PEPTIDE, VECTORS CONTAINING SAID NANOPARTICLES, AND PHARMACEUTICAL USES OF SAID NANOPARTICLES AND VECTORS

(75) Inventors: Louis Danicher, Strasbourg (FR); Yves Frere, Holtzheim (FR); Sylviane Muller, Strasbourg (FR); Anne Wawrezinieck, Orvault (FR)

(73) Assignees: CENTRE NATIONAL DE LA RECHERCHE SCIENTIFIQUE (C.N.R.S.), Paris (FR); UNIVERSITE DE STRASBOURG, Strasbourg (FR)

( * ) Notice: Subject to any disclaimer, the term of this patent is extended or adjusted under 35 U.S.C. 154(b) by 472 days.

(21) Appl. No.: 12/993,664

(22) PCT Filed: May 20, 2009

(86) PCT No.: PCT/FR2009/050944
§ 371 (c)(1),
(2), (4) Date: May 10, 2011

(87) PCT Pub. No.: WO2009/150371
PCT Pub. Date: Dec. 17, 2009

(65) Prior Publication Data
US 2011/0223242 A1 Sep. 15, 2011

(30) Foreign Application Priority Data

May 20, 2008 (FR) ..................... 08 53264

(51) Int. Cl.
| A61K 9/51 | (2006.01) |
| C07K 14/47 | (2006.01) |
| A61K 38/00 | (2006.01) |

(52) U.S. Cl.
CPC ......... *C07K 14/4713* (2013.01); *A61K 9/5161* (2013.01); *A61K 9/5169* (2013.01); *A61K 38/00* (2013.01)

(58) Field of Classification Search
CPC ........ A61K 9/14; A61K 9/51; A61K 9/5161; A61K 38/00; A61K 38/16
See application file for complete search history.

(56) References Cited

U.S. PATENT DOCUMENTS

| 5,571,531 A * | 11/1996 | McDermott et al. ......... 424/459 |
| 2003/0186849 A1* | 10/2003 | Zimmer ........................... 514/7 |
| 2003/0211166 A1* | 11/2003 | Yamamoto et al. .......... 424/493 |
| 2006/0216354 A1 | 9/2006 | Frere et al. |

FOREIGN PATENT DOCUMENTS

| WO | WO03/020747 | 3/2003 |
| WO | WO03/025014 | 3/2003 |

OTHER PUBLICATIONS

Mishra et al. "Biodegradable Polymer Based Particulate Carrier(s) for the Delivery of Proteins and Peptides", Anti-Inflammatory & Anti-Allergy Agents in Medicinal Chemistry, Dec. 2008, pp. 240-251.*
Monneaux et al., "Importance of spliceosomal RNP1 motif for intermolecular T-B cell spreading and tolerance restoration in lupus", Arthritis Research & Therapy, 2007, pp. 1-10.*
Monneaux et al., "Selective Modulation of CD4+ T Cells from Lupus Patients by a Promiscuous, Protective Peptide Analog", The Journal of Immunology, 2005, pp. 5839-5847.*
F. Monneaux et al., Intramolecular T Cell Spreading in Unprimed MRL/lpr Mice, Importance of the U1-70K Protein Sequence 131-151, Arthritis & Rheumatism vol. 50, No. 10, Oct. 2004, pp. 3232-3238.
G. Sandri et al., Mucoadhesive and penetration enhancement properties of three grades of hyaluronic acid using porcine buccal and vaginal tissue, Caco-2 cell lines,and rat jejunum, Journal of Pharmacy and Pharmacology, vol. 56, No. 9, 2004, pp. 1083-1090.
International Search Report and the Written Opinion from corresponding PCT Application No. PCT/FR2009/050944, Oct. 12, 2009.
Monneaux et al., "T Cell Recognition and Therapeutic Effect of a Phosphorylated Synthetic Peptide of the 70K SNRNP Protein Administered in MRL/LPR Mice," European Journal of Immunology, 33:287-296 (2003).
Pauletti et al., "Improvement of Oral Peptide Bioavailability: Peptidomimetics and Prodrug Strategies," Advanced Drug Delivery Reviews, 27:235-256 (1997).

* cited by examiner

*Primary Examiner* — Lianko Garyu
(74) *Attorney, Agent, or Firm* — Blank Rome LLP

(57) ABSTRACT

The present invention relates to nanoparticles containing a P140 peptide and to carriers, with or without dispersant, containing the nanoparticles. The present invention also relates to pharmaceutical and therapeutic uses of the nanoparticles, in particular for the treatment of systemic lupus erythematosus.

14 Claims, No Drawings

NANOPARTICLES CONTAINING A PEPTIDE, VECTORS CONTAINING SAID NANOPARTICLES, AND PHARMACEUTICAL USES OF SAID NANOPARTICLES AND VECTORS

RELATED APPLICATIONS

This application is the U.S. National Stage of International Application No. PCT/FR2009/050944, filed May 20, 2009, which claims the benefit of French Application Ser. No. 0,853,264, filed May 20, 2008.

The present invention relates to nanoparticles containing a peptide and to carriers, with or without dispersant, containing said nanoparticles. The present invention also relates to pharmaceutical and/or therapeutic uses of said vectors, in particular for the treatment of systemic lupus erythematosus.

The Sequence listing in "087927-0011-SL.TXT" created on May 5, 2011, being 4.00 KB in size is incorporated by reference.

Systemic lupus erythematosus (SLE) is a highly debilitating chronic inflammatory autoimmune disease which currently affects several million people throughout the world. This disease results from a malfunction of the immune system which recognizes self elements as non-self elements and then develops an immune response including that of producing antibodies against the organism's own constituents.

One promising therapeutic approach is based on the use of peptide sequences derived from autoantigens which can modulate the autoimmune response by interfering with the production of the autoantibodies. In this regard, the international application WO 03/025014 describes the use of specific peptides in the context of treating systemic lupus erythematosus. More particularly, this international application describes the use of the peptide P140, which is an analog phosphorylated on the serine residue in position 140 of the peptide 131-151 of the spliceosomal protein U1-70K (specific protein of the particle U1-snRNP), in particular in the context of treating systemic lupus erythematosus.

At present, the peptide P140 is administered by subcutaneous injection, which is not a comfortable mode of administration for the patient. Several other modes of administration have thus been tested. For instance, intranasal administration has been tested in mice but is not effective.

In the therapeutic domain, the most common ways of administering active principles are orally, intravenously, intramuscularly or subcutaneously. However the oral route, which is the most physiological and the most comfortable for the patient, cannot be used for many active substances such as peptides or proteins. This is because these macromolecules of the peptide or protein type are subject to many attacks along the gastrointestinal tract which alter their structure and their biological function. Furthermore, their passage through the intestinal wall is limited by their size and their hydrophilic nature. All of this explains the low bioavailability of proteins administered orally (around 1 to 2%).

One of the aims of the present invention is therefore to improve the efficacy of the aforementioned peptide P140 in the context of oral administration.

Another aim of the present invention is to provide the peptide P140 in encapsulated form which can be administered orally and which makes it possible to reach the same type of cells with the same efficacy as when the peptide is administered subcutaneously.

The aim of the present invention is therefore to provide a system for oral administration of the aforementioned peptide P140 which has characteristics of availability of said peptide that are comparable with the characteristics of direct injection of said peptide into the blood.

Another aim of the invention is to provide an administration system which allows the release of said peptide in a form that is denatured or degraded only a little, if at all, when administered orally.

Another aim of the invention is to provide an administration system which enables said peptide to reach and/or pass through the intestinal wall without being substantially denatured or degraded.

Another aim of the invention is to provide an administration system which makes it possible for said peptide, having passed through the intestinal wall, to be available in the blood, optionally after passing into the interstitial fluid.

Another aim of the invention is to provide a system for oral administration of the peptide P140 in which said peptide is not or is only slightly denatured or degraded when passing along the gastrointestinal tract and when passing through the intestinal wall, and which permits an immediate, delayed or extended availability in the blood.

The present invention relates to nanoparticles comprising a matrix consisting of at least one polysaccharide and of the peptide P140 having the sequence SEQ ID NO: 1 or one of the analogs thereof, said polysaccharide preferably being a polysaccharide carrying one or more negatively charged functional groups.

The peptide P140 is a peptide consisting of 21 amino acid residues having a molar mass of 2636 Da which corresponds to the following sequence: RIHMVYSKRSGKPRG-YAFIEY, in which the serine in position 10 is phosphorylated (SEQ ID NO: 1).

The expression "analogs of the peptide P140" denotes peptides comprising the aforementioned sequence SEQ ID NO: 1 in which at least one of the amino acids comprises a modification of the post-translational type, in particular by phosphorylation or acetylation. Among the analogs, reference may be made to the peptides described in the international application WO 03/025014.

The expression "one or more negatively charged functional groups" denotes chemical functions such as carboxyl groups for example.

The polysaccharide constituting the matrix must be biocompatible, biodegradable and bioassimilable (metabolizable).

According to another embodiment, the nanoparticles according to the invention may be prepared from a matrix consisting of a mixture of polysaccharides and of the peptide P140. More particularly, these nanoparticles may comprise a matrix consisting of the peptide P140 and of a mixture of hyaluronic acid and chitosan.

According to one particularly advantageous embodiment, the nanoparticles according to the invention are obtained by complex coacervation between the peptide and the polysaccharide.

According to one advantageous embodiment, the nanoparticles according to the present invention comprise a matrix consisting of hyaluronic acid.

Hyaluronic acid is non-toxic, biocompatible and metabolizable since it is present in many tissues.

In this embodiment, the nanoparticles are obtained by complex coacervation between the peptide P140 and hyaluronic acid.

Preferably, the size of the nanoparticles according to the invention is from around 1 nm to around 10 μm.

According to one particularly advantageous embodiment, in the nanoparticles according to the present invention, the weight ratio between the polysaccharide and the peptide is from around 0.1 to around 10, and in particular from around 0.5 to around 5, and preferably equal to around 1.

This weight ratio influences the ratio between the positive and negative charges present in the solution.

It has been found that the value of this weight ratio influences the size of the nanoparticles obtained.

Preferably, when the polysaccharide is hyaluronic acid, this ratio is equal to around 1 (1.5 negative charge for 1 positive charge), which then makes it possible to ensure colloidal stability. When this ratio is equal to 1, spherical nanoparticles having a diameter close to 200 nm and a negative surface charge ($\xi=-30$ mV) are obtained, which can easily be centrifuged and which are stable for several weeks at 4° C.

The nanoparticles that are preferred according to the present invention are nanoparticles as defined above in which the molar mass of the polysaccharide is from around 1000 Da to around 1 500 000 Da, and preferably from around 15 000 Da to around 50 000 Da, and in particular from around 20 000 Da to around 30 000 Da.

Preferably, the nanoparticles are prepared from hyaluronic acid having a molar mass equal to 27 600 Da. In this case, the nanoparticles obtained have a size close to 200 nm and are perfectly spherical. They are then also very monodisperse with a polydispersity index less than 0.1. These particles can be isolated from the synthesis medium by centrifugation at a speed of 2370 G without any problem of aggregation. They have a negative surface charge with a zeta potential of around −30 mV. Most of their surface is covered with hyaluronic acid and the peptide P140, of positive charge, condensed in the interior, is protected from the external environment by this polyelectrolyte. This surface charge ensures a good stability of the suspension during storage (at least two weeks at 4° C.) and during centrifugation.

The present invention also relates to a complex vector for oral administration, consisting of a carrier which comprises at least one nanoparticle as defined above.

The nanoparticle and the carrier are two vectors, the first having the aim of enabling the peptide to pass through the intestinal barrier and the second having the aim of enabling the nanoparticle to pass through the gastric fluid. These two vectors together form a complex vector.

The administration of the peptide P140 (or analog) via the oral route consists in fact of moving said peptide from the mouth into the blood or tissues without said peptide being substantially denatured or degraded. The intention is therefore that the dose of peptide P140 (or analog) administered orally must be able to be found substantially qualitatively and quantitatively in the blood or tissues. "Substantially qualitatively and quantitatively" is understood to mean that the quantity of peptide P140 (or analog) in the blood or tissues compared to the quantity of P140 (or analog) administered orally must be advantageously greater than at least 20%, in particular greater than 50%, preferably greater than 65%, advantageously greater than 80% and optimally greater than 90%.

Preferably, the nanoparticle contained in the complex vector as defined above is bioassimilable or metabolizable at a pH from around 6 to around 8, in particular from around 6.7 to around 7.7, and preferably from around 7.2 to around 7.5.

When administered orally, the substance that is active from the pharmacological point of view (peptide P140 or analog) must overcome all the obstacles present in an organism before reaching the blood flow or the tissues, and must do so without undergoing substantial denaturations or degradations. The main obstacles and difficulties taken into account in the context of the present invention are first of all the passage of the active substance into the stomach, the sojourn in the intestinal lumen, the adhesion to the microvilli present in the intestine, and the passage from the intestine into the blood, optionally via the interstitial fluid.

The active substance (peptide P140 or analog) administered orally must reach the blood or the interstitial fluid or the tissues without substantial denaturation or degradation.

Considering that the characteristics of the blood and of the interstitial fluid are different from the other organs (the stomach and the intestine among others) through which the peptide passes from the buccal cavity, the inventors have devised a vector for the peptide P140 (or analog), which vector can be biocompatible and bioassimilable or metabolizable.

This vector must therefore be hydrophilic so as to be compatible with the various body fluids (lymphatic fluid, interstitial fluid, blood, etc.). The vector must also release rapidly, or in an extended or delayed manner, the peptide P140 at a pH of between around 6.7 and 7.7, ideally between around 7.2 and 7.5, so as to enable the peptide P140 to then be available in the blood, through the vector and/or after the degradation of the latter.

Without entering into complex mechanistic considerations, it is envisaged that the vector is degraded by the enzymes present in the surrounding environment (lysozyme, esterases, glycosidases, etc.). The degradation of the vector will allow the immediate, extended or delayed release of the peptide P140 into the interstitial fluid so as to reach the blood flow or the tissues. Once in the blood, the peptide P140 will interact with the sites of interest, or will be transported to the sites or organs, so as to produce the desired pharmacological effect.

In addition, this vector must be optimized so that its hydrophilic nature is modified in order to make it compatible with the wall of the intestine. This is because the wall of the intestine covered with a mucus is an essentially lipophilic environment, the pH of which is greater than around 7.8. It is therefore appropriate to modify the vector described above so that it is essentially lipophilic close to and on the intestinal wall, so that it has a relatively good mucoadhesion and finally so that it withstands the enteric environment (basic environment having a pH greater than around 7.8, presence of degradation enzymes, etc.).

According to one advantageous embodiment, the complex vector according to the present invention has its largest dimension from around 10 nm to around 2.5 cm, preferably from around 100 nm to around 1 cm and in particular from around 0.5 mm to around 2 mm.

It is also appropriate that the vector (nanoparticle) present in the intestinal lumen has a size and a shape allowing the physical passage of said vector through the intestinal membrane.

A size smaller than around 10 nm is also less preferred, the quantity of active substance transported by the vector possibly being too low. This is because the size of the nanoparticle vector is limited by the site of passage of the nanoparticle (paracellular route, transcellular route, lymphatic route).

The present invention also relates to a complex vector as defined above, in which the carrier is in the form of spheres having a diameter from around 10 nm to around 2.5 cm, preferably from around 100 nm to around 1 cm, and in particular from around 0.5 mm to around 2 mm.

The shape of the vector (nanoparticle) has no specific importance per se as long as it allows an easy passage through the intestinal wall. The vector may thus be in any known shape, for example sphere, spaghetti, ovoid, etc.

When the complex vector is in the form of spheres, this vector can be prepared by the conventional techniques for encapsulating active substances, such as, for example, by simple or complex coacervation, interfacial polycondensation, spray-drying, spray-coating, etc.

The vector (nanoparticle) according to the present invention comprises a matrix containing the peptide P140. In this regard, the matrix may be designed in the form of a gel containing said peptide or one of the analogs thereof. According to another aspect, the matrix is in the form of a sphere containing said peptide or one of the analogs thereof. Other shapes are also envisageable, for example shapes of the "sponge" type, or any other solid shapes that are more or less compact and that can release by diffusion and/or after degradation the one or more active substances (peptide P140 or one of the analogs thereof) contained therein.

It must be specified that, besides the one or more active substances, the vector (nanoparticle) may also contain any excipient, filler, dye and other suitable substances known to the person skilled in the art, and non-toxic from the pharmacological point of view.

According to one particularly advantageous embodiment, the complex vector according to the invention comprises a carrier intended for gastric protection.

In order to be pharmacologically effective, this complex vector intended to be administered orally must also have a high resistance to the stomach environment through which it will pass before reaching the intestine. The stomach is an organ in which the pH is highly acidic (around 2, or even less). In addition, the enzymes present (in particular pepsin) in the stomach may denature, damage or even completely destroy said vector and hence the one or more active substances contained therein.

It is therefore desirable to provide gastric protection to the vector defined above. Gastric protection of the vector is understood to mean any carrier capable of protecting said vector against the physiological stresses inherent in the stomach, these stresses being mainly the acidic pH and the stomach enzymes (pepsin). Of course, the constituents of the carrier and also the denaturation or degradation products thereof must be non-toxic to the organism and biotolerated.

Such carriers are already widely known in the field (encapsulated medicaments for example, as described in "Encyclopedia of Pharmaceutical Technology", Marcel Dekker, (1992), J. Swarbrick and J. C. Boylan Editors, *Enteric Coatings*, pp. 189-200). Any gastro-resistant carrier known to the person skilled in the art can therefore be used. Preferably, it may be solid in nature, in the form of a gel, or may be in the form of a coating or a capsule, and may contain one or more vectors as defined above which are in turn in various forms, capsules, gels or others.

According to one preferred aspect of the present invention, the gastro-resistant carrier is in the form of a capsule containing one or more vectors as defined above. Said carriers in the form of a capsule may advantageously be obtained by methods of the coacervation, interfacial polycondensation in dispersed medium or other type. Of course, any other known method of encapsulation may be used and/or adapted with a view to preparing the carriers of the invention.

Among the constituents capable of withstanding the physiological stresses inherent in the stomach, mention may be made in particular of alginates, such as calcium alginate, carboxymethylcellulose, and others, as well as mixtures thereof. The gastro-protective carrier will have to withstand an acidic pH, in particular less than 2 and more particularly less than 1.2, and also attacks from the gastric enzymes.

Of course, the constituents of the carrier must have as characteristics the ability to be specifically modified or degraded in the intestinal lumen, that is to say at a pH greater than around 7.8 and in the presence of the enteric enzymes, so as to release the vector (nanoparticle) in the intestinal lumen.

One particular complex vector according to the present invention is a complex vector in which the carrier is in the form of a spherical matrix.

Preferably, the complex vector is in the form of spheres having a diameter of around 1.5 mm.

In the context of the present invention, the carrier as defined above may be in the form of a spherical capsule.

According to one particularly preferred embodiment, when the carrier is in the form of a spherical matrix or a spherical capsule, this is alginate-based, in particular in the form of an alginate sphere or capsule.

In the context of the present invention, the carrier may be in the form of a spherical matrix obtained by extruding a solution of sodium alginate in a bath of $CaCl_2$.

Furthermore, all biocompatible, bioassimilable and/or metabolizable gelling polymers may be used to form the spherical matrices or spherical capsules.

The present invention also relates to a complex vector as defined above, in which the carrier contains a lipophilic dispersant.

In addition, the gastro-resistant carrier may optionally contain a lipophilic medium, in which the one or more vectors (nanoparticles) defined above are present. This lipophilic medium may be in solid or liquid form or else in the form of a gel. The lipophilic medium may consist of any lipophilic compound that is known per se and non-toxic from the pharmacological point of view. The lipophilic compound envisaged may for example be selected from organic or mineral, plant or animal oils, for example olive oil, cod liver oil, silicone oils, and others, and also mixtures thereof.

Preferably, the aforementioned lipophilic dispersant is selected from the group consisting of organic or mineral, plant or animal oils, and mixtures thereof.

Advantageously, the aforementioned lipophilic dispersant is a mixture of fatty acid esters, in particular selected from the group consisting of caproic, caprylic, capric, lauric, myristic, linoleic and succinic acids.

The present invention also relates to a pharmaceutical composition comprising at least one nanoparticle as defined above or at least one complex vector as defined above, in combination with a pharmaceutically acceptable carrier.

The present invention also relates to the use of at least one nanoparticle as define above or at least one vector as defined above, as a medicament.

The present invention also relates to the use of at least one nanoparticle as defined above or at least one complex vector as defined above, for preparing a medicament intended for the treatment of autoimmune diseases, and in particular systemic lupus erythematosus.

The present invention relates to a nanoparticle as defined above for use for the treatment of autoimmune diseases, and in particular systemic lupus erythematosus.

The present invention also relates to a complex vector as defined above for use for the treatment of autoimmune diseases, and in particular systemic lupus erythematosus.

EXPERIMENTAL PART

Preparation of HAP140 Nanoparticles

HAP140 nanoparticles are nanoparticles obtained by complex coacervation between hyaluronic acid (HA) and the peptide P140.

Hyaluronic acid (5.2 mg; CERMAV Grenoble, France-molar mass 27 600 Da) is dissolved in 25 ml of bidistilled water and left with stirring for 24 hours to ensure a good dissolution of the HA polymer. The peptide P140 (200 µg) is weighed out on a microbalance and then dissolved in 250 µl of bidistilled water (pH 5.5). It is then added dropwise using a micropipette to the hyaluronic acid solution (1.05 ml; pH 6.5) in a test tube equipped with a small magnetized bar rotating at 250 rpm. The hemolysis tube containing the peptide is washed with 50 µl of bidistilled water which are then added to the suspension.

The addition of the peptide P140 to the hyaluronic acid is accompanied by the gradual formation of a cloudiness in the solution. After 15 minutes of stirring, the suspension is transferred into a 1.5 ml microtube and kept at 4° C. Since no aggregate has formed, no filtration step is necessary.

The nanoparticles thus obtained have the following properties (size distribution and polydispersity index):

| HA | Size (nm) | % in number | Polydispersity index |
|---|---|---|---|
| 27 600 Da | 220 | 100 | 0.07 |

These nanoparticles are perfectly spherical (Fig. 1—image of the HAP140 nanoparticles obtained, taken by means of transmission electron microscopy) and very monodisperse.

Preferably, these nanoparticles are isolated 24 hours after the synthesis thereof so as to ensure a good efficacy of encapsulation and then are stored for one week at 4° C. in bidistilled water so as to reach their thermodynamic equilibrium and so as to be stable in saline medium and in simulated intestinal fluid.

Administration of HAP140 nanoparticles to BALB/c mice

Once the synthesis of the HAP140 nanoparticles had been developed, it was checked that the peptide retains its integrity when it is condensed by hyaluronic acid in the form of nanoparticles.

It has been demonstrated that the peptide P140 is immunogenic when it is administered in the presence of adjuvant to BALB/c mice. In order to check that the peptide P140 is still recognized by the cells of the immune system, in particular the T cells, when it is in the form of particles, it was chosen to administer the HAP140 nanoparticles in the presence of adjuvant to BALB/c mice and to compare the immune response induced by the administration of HAP140 nanoparticles in the presence of adjuvant to that obtained with an administration of free peptide P140.

1. Development of the Immune Response

When an antigen enters the organism, it is detected and then internalized by the dendritic cells and macrophages present on the site of infection (or administration). These cells become mature and join the vessels of the lymphatic system in which the lymph that transports waste and foreign bodies flows. They are routed to the lymph nodes, secondary lymphoid members colonized by B and T lymphocytes. It is at these lymph nodes draining the site of infection (or immunization) that the immune response develops and that the T cells are activated following the presentation of the antigen by the dendritic cells or other antigen-presenting cells.

Most proteins or peptides such as P140 are not very immunogenic when they are administered alone in the absence of components representing danger signals. In order to obtain a strong immune response directed against a protein antigen, it is therefore necessary to administer it in the form of a mixture with an adjuvant. Most adjuvants contain killed bacteria or bacterial components which stimulate the macrophages and encourage the immune response. The adjuvant used here is complete Freund's adjuvant (CFA). This is an oil containing dead mycobacteria which not only facilitate the presentation of the antigen by the macrophages or dendritic cells but also induce the production of inflammatory cytokines and strong local inflammatory reactions.

2. Subcutaneous Administration of the HAP140 Nanoparticles

The subcutaneous (s.c.) administration of peptide P140 in the presence of adjuvant to BALB/c mice leads to the activation of the auxiliary T cells Th [Monneaux, F., Lozano, J. M., Patarroyo, M. E., Briand, J. P., and Muller, S. (2003) T cell recognition and therapeutic effect of a phosphorylated synthetic peptide of the 70K snRNP protein administered in MRL/lpr mice. Eur. J. Immunol. 33, 287-296]. This activation is demonstrated by analyzing the proliferation and production of cytokines of the T cells present in the lymph nodes draining the site of administration, stimulated ex vivo with the peptide P140.

a) Protocol

Female BALB/c mice aged 7 weeks old (4 groups of two mice) are immunized subcutaneously in the flanks with different formulations. The first group received the peptide P140 in the presence of CFA (control group), the second group received the HAP140 nanoparticles in the presence of CFA, the third group received the HAP140 nanoparticles in saline medium (in order to check that the HAP140 particles do not themselves have an adjuvant nature), and the fourth group received the "blank" HACS nanoparticles in the presence of CFA (in order to check the specificity of the response induced compared to the peptide P140). The mice having received peptide in its free form or in the form of nanoparticles all received the same quantity of peptide, namely 100 µg per mouse.

One week after the immunization, the mice are sacrificed and samples are taken from the lymph nodes of the flank and of the foreleg. The cells issuing from these lymph nodes are cultured ex vivo in a proportion of $5.10^5$ cells per well in the presence of different peptide concentrations (0, 6, 20 and 60 µM) so as to study their proliferation and also the secretion of cytokines.

Cytokines are proteins of low molar mass produced by many cell populations, including the lymphocytes. They can be described as the "hormones" of the immune system since they are involved in the relationships between the lymphocytes, macrophages and other cells. The functions thereof are wide-ranging: they can influence the survival, the proliferation, the differentiation or even the migration of cells.

The Th cells are classified into sub-populations, Th1 or Th2, depending on the cytokines that they produce and the function that they perform. Cells of type Th-1 produce in particular interleukin-2 (IL-2) and interferon-γ (IFN-γ), whereas cells of type Th-2 secrete essentially IL-4, IL-5, IL-6, IL-10 and IL-13. The immunization conditions used here, that is to say the use of CFA, encourage the development of a response of type Th1. Therefore, only the secretion of IL-2 and IFN-γ was studied.

If the immunization has been effective, the Th cells of the lymph nodes draining the site of immunization will be activated and will proliferate and secrete cytokines in the presence of peptide P140.

b) Results

Two formulations, the peptide in the presence of adjuvant and the HAP140 particles in the presence of adjuvant, gave positive and dose-dependent stimulation indices, which indicates a specific proliferative response of the peptide P140. The stimulation indices associated with the particles administered in saline solution remain very low by comparison, while those associated with the "blank" particles are negative.

The cytokine secretion results confirm the proliferation results: two dose-dependent responses were obtained in the case of the administration of the peptide and of the HAP140 nanoparticles both injected in the presence of CFA. The particles administered alone lead only to the production of a low quantity of IL-2 which is not dose-dependent and probably not significant, and do not lead to any production of IFN-γ. The administration of "blank" particles does not induce the secretion of any cytokine.

The peptide is therefore released from the HAP140 nanoparticles in its native form since the subcutaneous administration thereof in the presence of CFA gives rise to the same specific response as the administration of the free peptide in the presence of CFA. The stimulation indices obtained and also the secreted cytokine concentrations are similar for both of these. It therefore appears that all of the peptide condensed in the particles is preserved after subcutaneous administration to mice.

In addition, it is demonstrated that hyaluronic acid has no adjuvant nature, the co-administration of CFA being necessary in order to obtain dose-dependent responses. This is very important since, in the context of establishing therapeutic protocols in lupic mice, any adjuvant effect must be ruled out since it would have the potential consequence of accelerating the progression of the disease [Monneaux, et al. (2003) *Eur. J. Immunol.* 33, 287-296].

Finally, the administration of "blank" HACS particles does not generate any immune response, thus demonstrating that the measured response is indeed specific to the peptide P140 and not to the particles alone.

3. Intra-Duodenal Administration of HAP140 Nanoparticles

According to the results obtained in the preceding paragraph, the formation of HAP140 nanoparticles takes place under conditions that are not degrading for the peptide and the latter is released in its native form into the organism after subcutaneous administration. However, this route of administration is far-removed from the envisaged route of administration, namely the oral route.

In the complex pharmaceutical vector described above, the nanoparticles are protected by an acid-resistant carrier in the stomach and then released in the intestine so as to pass through the intestinal epithelium. In order to mimic the use of this vector, the nanoparticles are administered into the initial segment of the small intestine, the duodenum. This route of administration makes it possible to check that the nanoparticles are stable in intestinal fluid, that the peptide is protected against enzyme attacks and that at least a fraction thereof passes intact through the intestinal barrier.

a) Protocol

Female BALB/c mice aged 7 weeks old are immunized with different formulations by different routes of administration. The first group received the peptide P140 in the presence of CFA via the subcutaneous route, the second group received the HAP140 nanoparticles in the presence of CFA via the intra-duodenal route and the third group received the "blank" HACS nanoparticles in the presence of CFA via the intra-duodenal route. The mice having received peptide, either in its free form or in the form of nanoparticles, all received the same quantity of peptide, namely 100 µg per mouse, regardless of the route of administration used.

The immunization via the intra-duodenal route is carried out under anesthesia. A minor incision is then made in the abdomen in order to extract the upper segment of the intestine from the abdominal cavity and to carry out the administration into the duodenum. The incision is then sewn up again and the animal is kept beneath a heat lamp until it wakes up.

One week after the immunization, the mice are sacrificed and samples are taken from the lymph nodes draining the site of administration. In the case of intra-duodenal administration, these are the mesenteric lymph nodes which form a chain along the intestine and drain the intestinal mucosa. The cells issuing from these lymph nodes are cultured in the presence of different peptide P140 concentrations according to the protocol described in the preceding paragraph.

b) Results

The results obtained by the intra-duodenal route were superposed on those obtained above by the subcutaneous route in order to allow a comparison. It should be noted that the mesenteric lymph nodes of the mice that received the HAP140 particles in the presence of CFA via the intra-duodenal route are hypertrophic, a sign that they have been the site of an immune response.

The proliferation of the cells issuing from the mice immunized with the HAP140 particles via the intra-duodenal route in the presence of adjuvant is highly dose-dependent and the stimulation indices are of the same order of magnitude as those obtained by subcutaneous administration of the free peptide P140 in the presence of adjuvant. The stimulation indices associated with the "blank" HACS particles administered via the intra-duodenal route are not significant, regardless of the peptide concentration, a sign that the lymph node cells have not proliferated.

The intra-duodenal administration of HAP140 particles in the presence of adjuvant gives rise to a lower secretion of cytokines of type Th1 than in the case of subcutaneous administration. This is particularly obvious for IFN-γ. However, the secretions of IL-2 and IFN-γ remain dose-dependent and the cell proliferation indices are of the same order of magnitude as those obtained subcutaneously. The administration of HAP140 nanoparticles via the intra-duodenal route thus makes it possible to activate the Th cells of the mesenteric lymph nodes.

Thus the peptide is capable of effectively activating the Th cells, a sign that it is in native form. The particles will therefore be sufficiently stable in intestinal fluid in vivo to protect the peptide against enzyme attacks.

Therapeutic Protocol in Lupic MRL/lpr Mice by the Intra-Duodenal Administration of HAP140 Nanoparticles In order to study the therapeutic efficacy of the intra-duodenal administration of HAP140 nanoparticles, a therapeutic protocol was undertaken in lupic mice.

In order to study the therapeutic potential of the HAP140 nanoparticles, pre-lupic mice received three administrations of these particles via the intra-duodenal route in the absence of adjuvant, each spaced apart by two weeks. In order to allow a comparison of the progression of the disease and to study the efficacy of our nanoparticles, one group of mice received so-called "blank" HACS nanoparticles without peptide.

Protocol

Pre-lupic MRL/lpr female aged 5 weeks old at the start of the experiments were separated into two groups. The first group, consisting of 8 mice, received 100 µg of P140 in the form of HAP140 nanoparticles via the intra-duodenal route, and the second group, the control group, consisting of 5 mice, received 100 µg of chitosan in the form of HACS nanoparticles also via the intra-duodenal route. The first administration takes place at the age of 5 weeks and it is followed by two other administrations spaced apart by two weeks (that is to say at the age of 7 and 9 weeks). The symptoms of lupus disease, such as the onset of a proteinuria (presence of proteins in urine, measured on a urine strip), were regularly monitored for more than 45 weeks and a mortality profile was established.

Results

Intra-duodenal administration of HAP140 nanoparticles delays the onset of proteinuria in lupic MRL/lpr mice. In fact this symptom appears only at the age of 15 weeks in treated mice and 12 weeks in the group of untreated control mice. Their proteinuria also always remains less frequent than that developed by the control mice.

The administration of the HAP140 nanoparticles also appears to have a beneficial effect on the mortality of the treated animals. First of all, the administration significantly delays the start of the mortality curve. Although in the control group the first mice die at 15 weeks, the first mouse in the group that received the HAP140 nanoparticles did not die until 22 weeks. This difference is particularly interesting if it is considered that, according to the data contained in the literature, the life span of a lupic MRL/lpr mouse does not exceed 35 weeks.

These data are moreover confirmed in our study since, at the age of 37 weeks, all the mice in the control group are dead. Interestingly, 50% of the mice that received the nanoparticles are still alive at this age and are still alive at 45 weeks, that is to say a half-life of 25 weeks for the untreated mice compared to a half-life of 45 weeks for the treated mice.

The administration of HAP140 nanoparticles via the intra-duodenal route in pre-lupic mice therefore makes it possible to extend significantly the life span thereof.

Thus, the intra-duodenal administration of HAP140 nanoparticles makes it possible not only to delay the onset of the clinical signs of the disease such as proteinuria but also to extend the life span of the animals very significantly.

At least some of the particles or of the dose of peptide is therefore capable of passing through the intestinal barrier and of reaching the systemic circulation and/or the target cells.

Study of Passing Through the Intestinal Barrier

In order to study the passage of the nanoparticles through the intestinal wall, an in vitro model using a cancerous human cell line from the colon (Caco-2) was developed. These cells are capable of differentiating into enterocytes during the culture thereof, thus mimicking the layer of cells constituting the intestinal wall.

Observations using a transmission electron microscope have made it possible to demonstrate the differentiation of these cells after being cultured for 13 days (presence of villi and desmosomes). These cells contain many organelles having a size close to that of the synthesized nanoparticles, which makes them difficult to identify.

Observations by confocal microscopy were therefore carried out in order to observe the passage of the particles through this epithelium model. To this end, chitosan was coupled to fluorescein isothiocyanate (FITC) and $HACS_{FITC}$ nanoparticles were synthesized. These particles have characteristics (size, surface finish) similar to those of the HAP140 particles and can be obtained in a sufficient quantity for the envisaged studies. The observations by confocal microscopy demonstrated the presence of nanoparticles not only on the surface of the cells but also in the cytoplasm thereof. It has been demonstrated that the passage of the particles into the cells takes place by a mechanism that is probably active since it takes place at 37° C. but not at 4° C. Studies by flow cytometry have moreover demonstrated that the absorption of the particles takes place not only in a dose-dependent manner but also increases with the incubation period. The presence of nanoparticles in the cytoplasm of the Caco-2 cells was confirmed by transmission electron microscopy using an anti-FITC antibody coupled to gold beads.

However, this cellular model exhibits differences over an intestinal epithelium, such as the absence of mucus or of M cells. Fluorescent nanoparticles were therefore administered via the intra-duodenal route to lupic mice and intestinal slices were taken so as to observe the passage of these nanoparticles. A high fluorescence intensity is found in the intestinal lumen and in the mucus, which is known to trap the particles. Fluorescent particles are also detected inside the villi, as far as the basal membrane of the intestine. Thus, although most of the particles remain in the mucus, a non-negligible quantity thereof are capable of passing through the intestinal epithelium.

Synthesis of an Alginate-Based Acid-Resistant Carrier Containing a Pharmaceutical Oil 1. Protocol for Synthesis of the Carrier Principle of the Synthesis The protocol used to obtain such a carrier is as follows: finely ground calcium carbonate is dispersed in a pharmaceutical oil of MIGLYOL® type. This suspension is added dropwise at a rate of 20 ml/h through a syringe equipped with a stainless steel needle (diameter of the needle 0.9 mm) to a bath of sodium alginate containing glacial acetic acid. In contact with this acidic solution, the calcium carbonate will release calcium ions at the oil/water interface, which will then complex with the alginate and form a membrane around each droplet of oil. The capsules thus obtained will therefore have a size of a few millimeters, close to that of the droplet of oil formed at the outlet of the needle.

100 ml of a 0.5% (w/v) alginate solution of very low viscosity containing 1% (v/v) glacial acetic acid are poured into a small 250 ml reactor equipped with a mechanical stirrer in the shape of an anchor. The calcium carbonate (500 mg) is finely dispersed in 5 ml of MIGLYOL® 829 (density 1 to 1.02). This dispersion is then added dropwise through a syringe equipped with a stainless steel needle (diameter of the needle 0.9 mm) to acidic alginate solution at a constant rate of 20 ml/h. Once the addition is complete, the system is left with stirring at 150 rpm for one hour in order to give the calcium ions time to migrate towards the aqueous solution and to complex the alginate on the surface of the droplets of oil. The carriers are then diluted in a large volume of water to facilitate their filtration through a filtration system, for example Millipore(3 µm). In order to reinforce the crosslinking of the alginate, they are then immersed in a solution of calcium chloride for 30 min and then kept at 4° C. in water. Spherical carriers having a diameter of between 1.5 mm and 2 mm and having a membrane thickness close to 500 µm are thus obtained.

2. Stability of the Carrier in Reconstituted Physiological Media

The stability of these carriers was evaluated in simulated gastric and intestinal fluids. We studied more particularly the influence of the duration of synthesis of the carriers (duration of contact of the droplets of oil containing calcium carbonate with the acidic alginate solution) on the stability thereof.

The immersion of these carriers in simulated gastric fluid leads to a reduction in thickness of their alginate membrane that is visible to the naked eye. This phenomenon is similar to that observed for the first type of carrier developed in this chapter: at acidic pH, the alginate precipitates as alginic acid, which is accompanied by a retraction of the gel. The membrane of the carriers brought into contact with the alginate for at least 30 min remains intact after 4 hours of immersion in simulated gastric fluid. This is not the case for the carriers having a duration of synthesis less than 15 minutes: the thin alginate capsule thus obtained splits and releases its contents, namely the oil, in this acidic medium. The carriers must therefore be kept in the alginate bath for at least 30 minutes in order to be stable for 4 hours in simulated gastric fluid.

When the carriers are transferred into simulated intestinal fluid, a very rapid splitting of the membranes of the carriers is observed, these having been thinned as a result of their sojourn in acidic medium. In less than 30 minutes, all the carriers are degraded and all of the oil is released into the medium. The degradation is all the more rapid the less time the carriers have remained in contact with the alginate solution during their synthesis. For instance, carriers immersed for 1 hour in the alginate bath degrade in 30 minutes in simulated intestinal fluid, whereas 5 minutes are enough to degrade all of the carriers immersed in this same alginate bath for just 30 minutes.

TABLE 1

Effect of the calcium alginate crosslinking duration on the stability of the resulting carriers in simulated gastric fluid and then in simulated intestinal fluid

| Alginate crosslinking duration | Stability in simulated gastric fluid (4 h) | Stability in simulated intestinal fluid |
| --- | --- | --- |
| 15 min | No | X |
| 30 min | Yes | 5 min |
| 45 min | Yes | 15 min |
| 1 h | Yes | 30 min |

It is therefore possible to vary the immersion time of the carriers in the alginate bath during the synthesis thereof in order to accelerate or slow the phenomenon of degradation observed in simulated intestinal fluid.

The degradation of the carriers in simulated intestinal fluid must be quick enough to take place in the upper segment of the intestine: if the degradation of the carrier does not take place early enough, the nanoparticles will remain trapped therein for part of their sojourn in the intestine and may not enter into contact with the intestinal epithelium. An incubation time of 30 to 45 min in the alginate bath appears to be optimal since it makes it possible to obtain carriers that are not only stable for 4 hours in gastric fluid but also appear to degrade rapidly (5 to 15 min) in simulated intestinal fluid.

This new carrier therefore performs two main functions in vitro: withstanding an acidic pH for 4 hours and thus protecting the nanoparticles during their passage through the stomach, and degrading rapidly in intestinal fluid so as to release said nanoparticles.

3.—Miniaturization of the Carrier—Preliminary Study

For the purpose of administering the complex vector orally to mice, it is necessary to miniaturize the carrier.

a) Principle of the Synthesis

The obtaining of small alginate capsules with an oily core is based on a simple modification of the protocol used above: an oil-in-water emulsion is obtained by homogenizing a suspension of calcium carbonate in MIGLYOL® 829 with an aqueous alginate solution. Adding glacial acetic acid to this emulsion makes it possible to initiate the migration of the calcium carbonate towards the alginate and the release of $Ca^{2+}$ cations, thus leading to the formation of crosslinked alginate membranes around each of the droplets of oil.

b) Synthesis Protocol $CaCO_3$ (100 mg) is dispersed in 1 ml of pharmaceutical oil MIGLYOL® 829, then this dispersion is homogenized in a 0.5% (w/v) alginate solution of very low viscosity. The emulsion is obtained using a homogenizer (ULTRA-TURRAX® T25 basik IKA® Werke) used at a speed of 600 rpm for 5 minutes. The glacial acetic acid (500 µl) is then added dropwise so as to initiate the release of the calcium cations and the formation of the alginate membrane around the droplets.

These conditions lead to the formation of spherical alginate capsules with an oily core, having a size of a few tens of µm.

Preparation of a Vector According to the Invention

The protocol for synthesizing a complex vector is identical to that of the carriers, replacing the pharmaceutical oil MIGLYOL® 829 with a dispersion of nanoparticles containing the peptide P140 (or analog) in pharmaceutical oil MIGLYOL® 829, the rest of the protocol remaining unchanged.

The invention claimed is:

1. A nanoparticle comprising a matrix consisting of at least hyaluronic acid and of a peptide P140 having the sequence SEQ ID NO: 1 or one of the analogs thereof, wherein the weight ratio between hyaluronic acid and the peptide is from about 0.1 to about 10.

2. The nanoparticle of claim 1, the size of which is from around 1 nm to around 10 μm.

3. The nanoparticle of claim 1, wherein the molar mass of the hyaluronic acid is from around 1000 Da to around 1 500 000 Da.

4. The nanoparticle according to claim 1 obtained by complex coacervation between the peptide and the hyaluronic acid.

5. A complex vector for oral administration, consisting of a carrier which comprises at least one nanoparticle according to claim 1, the carrier containing the nanoparticle.

6. The complex vector of claim 5, wherein the carrier is intended for gastric protection.

7. The complex vector of claim 6, wherein the carrier is in the form of a spherical matrix or a spherical capsule.

8. The complex vector of claim 7, wherein the carrier is alginate-based.

9. The complex vector of claim 6, wherein the carrier contains a lipophilic dispersant.

10. The complex vector of claim 8, wherein the carrier is in the form of an alginate sphere of capsule.

11. A pharmaceutical composition comprising at least one nanoparticle according to claim 1, in combination with a pharmaceutically acceptable carrier.

12. A pharmaceutical composition comprising at least one complex vector according to claim 5, in combination with a pharmaceutically acceptable carrier.

13. A method for treating systemic lupus erythematosus in an individual comprising the administration of a therapeutically effective amount of the nanoparticle of claim 1 to the individual in need thereof.

14. A method for treating systemic lupus erythematosus in an individual comprising the administration of a therapeutically effective amount of the complex vector of claim 5 to the individual in need thereof.

* * * * *

SEQUENCE LISTING

```
<160> NUMBER OF SEQ ID NOS: 1

<210> SEQ ID NO 1
<211> LENGTH: 21
<212> TYPE: PRT
<213> ORGANISM: Homo sapiens
<220> FEATURE:
<221> NAME/KEY: MOD_RES
<222> LOCATION: (10)..(10)
```

```
-continued

<223> OTHER INFORMATION: PHOSPHORYLATION

<400> SEQUENCE: 1

Arg Ile His Met Val Tyr Ser Lys Arg Ser Gly Lys Pro Arg Gly Tyr
1               5                   10                  15

Ala Phe Ile Glu Tyr
            20
```